United States Patent [19]
Fontirroche et al.

[11] Patent Number: 5,538,510
[45] Date of Patent: Jul. 23, 1996

[54] CATHETER HAVING COEXTRUDED TUBING

[75] Inventors: Carlos A. Fontirroche, Miami Springs; Stephen J. Querns, Boca Raton, both of Fla.

[73] Assignee: Cordis Corporation, Miami Lakes, Fla.

[21] Appl. No.: 189,209

[22] Filed: Jan. 31, 1994

[51] Int. Cl.$^6$ .............................. A61M 5/30; A61M 25/00
[52] U.S. Cl. .............................................. 604/265; 604/280
[58] Field of Search ................................... 604/280, 281, 604/282, 283, 93, 264, 265, 96

[56] References Cited

U.S. PATENT DOCUMENTS

| | | |
|---|---|---|
| 3,814,137 | 6/1974 | Martinez . |
| 4,923,450 | 5/1990 | Maeda et al. . |
| 4,994,047 | 2/1991 | Walker et al. ........................ 604/265 |
| 5,063,018 | 11/1991 | Fontirroche et al. .................... 264/514 |
| 5,120,323 | 6/1992 | Shockey et al. . |
| 5,195,969 | 3/1993 | Wang et al. ............................ 604/103 |
| 5,195,971 | 3/1993 | Sirhan . |
| 5,221,270 | 6/1993 | Parker .................................... 604/264 |
| 5,270,086 | 12/1993 | Hamlin . |
| 5,272,012 | 12/1993 | Opolski .................................. 604/265 |
| 5,290,306 | 3/1994 | Trotta et al. . |

FOREIGN PATENT DOCUMENTS

| | | |
|---|---|---|
| 0420488 | 4/1991 | European Pat. Off. . |
| 2130093 | 5/1984 | United Kingdom . |
| 2209121 | 5/1989 | United Kingdom . |

OTHER PUBLICATIONS

Quantum–Plexar–Tie–Layer Resins The Essential Bond for Coextruded Packaging, 8 pages.
Quantum–Plexar–Tie–Layer Resin–Designing Plexar Tie-Layer Resins with Low MVTR Properties, 4 pages, Jun. 1989.
Quantum–Plexar–Tie–Layer Resin–Evaluation of Plexar Tie–Layers for EVOH/PET Coextrusion, 2 pages, 1991.
Brochure of unknown date from Schneider Innovation for Life 2 pages.
Article by Norman G. Gaylord et al. entitled: "Maleation of Linear Low–Density Polyethylene by Reactive Processing-"–Gaylor Research Institute, New Providence, New Jersey 07974, pp. 1941–1949.
Article by Norman G. Gaylord entitled: "Compatibilizing Agents: Structure and Function in Polyblends" J. Macromol. Sci.–Chem., A26(B), pp. 1211–1229 (1989), Research Institute for Scientists Emeriti, Drew University, Madison, New Jersey 07940.

Primary Examiner—Randall L. Green
Assistant Examiner—Ronald K. Stright, Jr.
Attorney, Agent, or Firm—Gerstman, Ellis & McMillin, Ltd.

[57] ABSTRACT

An intravascular catheter comprises a length of flexible plastic tubing which, in turn, comprises an outer plastic layer and an inner plastic layer. The plastic materials of the outer and inner layers are different, and may be chemically bonded to each other. Advantages in catheter design are achieved.

18 Claims, 1 Drawing Sheet

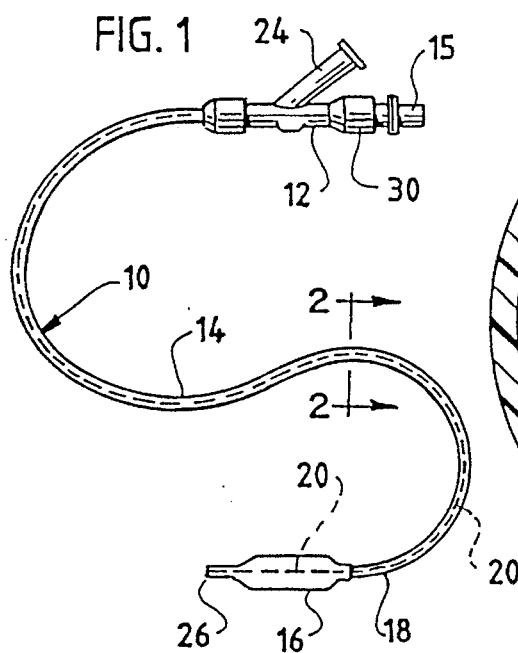
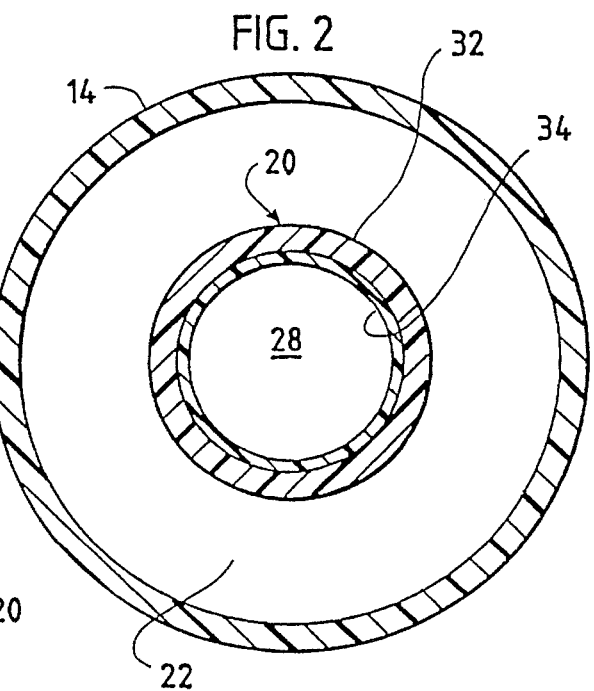
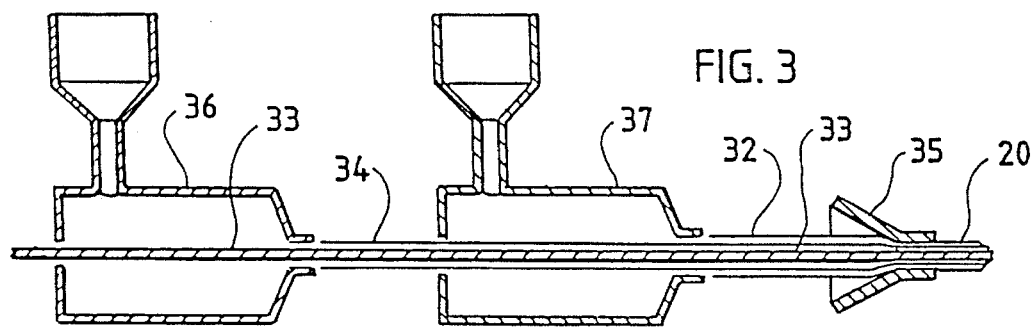
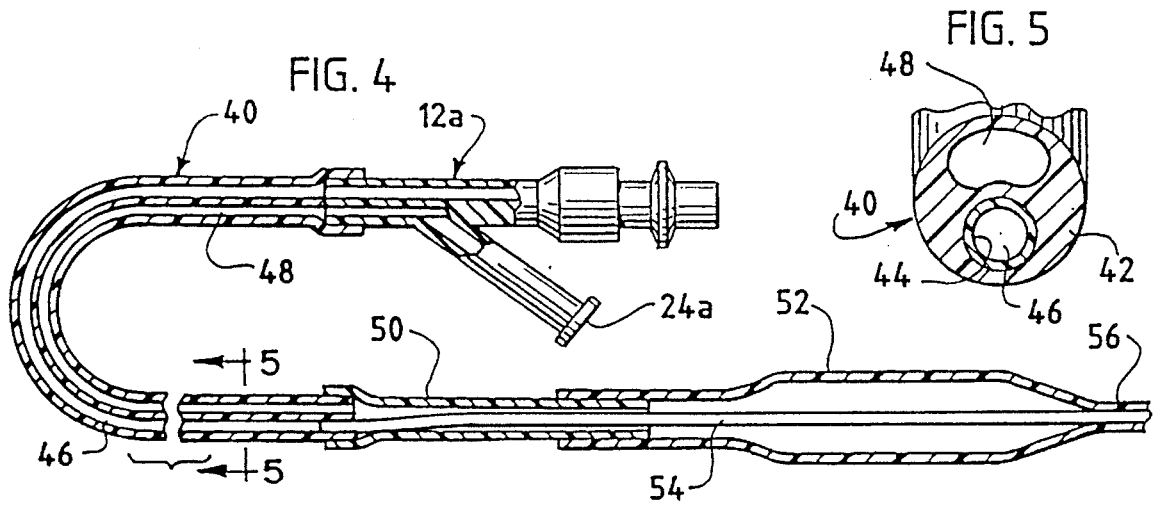
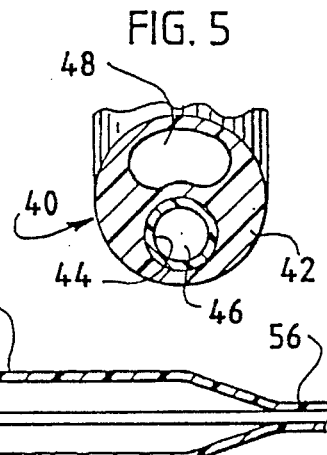

CATHETER HAVING COEXTRUDED TUBING

BACKGROUND OF THE INVENTION

Intravascular catheters, such as catheters for advancement into the arterial system around the heart, are presently in wide clinical use both for angiography and angioplasty (PTCA). As is well known, the catheter must be made of a flexible material which, nevertheless, exhibits a certain stiffness so that the catheter may be advanced through the various twists and turns of the arterial system to bring an angioplasty balloon or other clot opening device, for example, to the desired site of arterial occlusion. Also, while the plastic body of the catheter must exhibit this desired stiffness and other particular characteristics, the catheter lumen must have a low friction surface so that the catheter can be advanced along a guidewire, and also a guidewire or inner catheter can be advanced through the catheter lumen.

Conventionally, a catheter having a nylon body or a body of polyethylene, polyurethane, poly(ethylene terephthalate) (known as PET) is used, with the catheter lumen having a lubricating coating or containing a preformed polytetrafluoroethylene (PTFE) sleeve. This inner PTFE sleeve provides the desired low friction to the catheter lumen, while the balance of the catheter can provide other desired qualities. However, it has sometimes been found that the presence of the PTFE tubing can make the catheter too stiff, as well as unduly subject to kinking, when the catheter turns a sharp corner in the arterial system of the patient in which it is used.

PTFE is of course a stiff plastic, and this has to be accommodated for by reducing the thickness of the outer catheter layer by an amount that may cause other characteristics of the catheter to be less than optimum. Also, the PTFE of course does not bond in any significant way to the nylon or PET outer catheter layer. This provides an added possible disadvantage that the PTFE tubing may shift with respect to the outer catheter layer and slide out of the lumen to a certain extent. As is well known, PTFE bonds only with great difficulty to most other plastic materials.

If it were desired to replace the inner PTFE tubing in conventional catheters with another low friction plastic such as a high density polyethylene, this material also is incompatible with nylon, for example, and does not form a significant bond with nylon upon coextrusion of tubing with a nylon outer layer and a high density polyethylene inner layer. Such layers also can slip in their relative position because of the essential absence of a bond, even after coextrusion.

As another prior art expedient, the interior of a catheter is coated with a friction reducing material such as a silicone in liquid form, which is then dried. Such processes are particularly difficult with small diameter intravascular catheters. Also, silicone resins and the like which are used for such coating lack the best low friction characteristics to facilitate advancement of such catheters along a guidewire.

In accordance with this invention, a catheter is provided having tubing with inner and outer tubular layers which are bonded to each other for firm retention and ease of manufacture. The manufacturing may be simply by coextrusion, while obtaining the desired bond and other desired characteristics of the respective inner and outer catheter layers to optimize overall catheter performance.

DESCRIPTION OF THE INVENTION

By this invention, an intravascular catheter is provided which comprises a length of flexible plastic tubing. The tubing comprises an outer plastic layer and an inner plastic layer, the plastic materials of the outer and inner plastic layers being different, and covalently bonded to each other.

Preferably, the plastic material of the inner plastic layer defines a catheter lumen having the walls which exhibit lower frictional characteristics than the material of the outer plastic layer. Thus, the selection of the desired outer plastic layer materials for the catheter may be greatly broadened to optimize catheter performance. For instance, a material may be selected which bonds optimally to the desired balloon material of catheters which carry such balloons for good bonding, while the lumen of the catheter provides desired lumen characteristics, particularly low friction for a guidewire or a catheter advancing through the lumen.

Preferably, the material of the outer plastic layer has a greater stiffness than the material of the inner plastic layer, to provide a catheter which is flexible, but stiff enough for optimal "pushability" for advancement thereof, particularly into the arterial system of a patient adjacent the heart. For example, nylon, polyurethane, or PET may be used as the outer plastic layer material.

Preferably, a chemical bond is used between the outer and inner plastic layers in the catheter tubing.

The material of the inner plastic layer typically comprises a vinylic polymer having functional groups bonded to the material of the outer plastic layer. The vinylic polymer may be a copolymer having a major amount of ethylene units and a minor amount of units of unsaturated carboxylic acid or an anhydride thereof. Typically, known resins manufactured and sold by the Quantum Chemical Company under the trademark Plexar may be used for the inner plastic layer. These materials are vinylic (for example polyethylene of varying densities, polypropylene, or poly(ethylene vinyl acetate) which are copolymerized with a small amount of maleic acid. These materials have been used chiefly as "tie layers" for multilayer plastic sheeting, the Plexar material being an inner layer which bonds together dissimilar outer plastic layers. Other unsaturated carboxylic acids such as fumaric acid, cinnamic acid, crotonic acid, linoleic acid, or the like may also be used as a substitute for Maleic acid.

In accordance with this invention, a plastic material similar to Plexar or the like may be used as typically the inner layer of a multiple layer catheter tubing, taking advantage of the good chemical bonding power of the Plexar or other similar plastic, preferably without using the functional plastic material to bond two dissimilar layers together, but making use of the material in its own right for its desired characteristics. For example, high density polyethylenes which have been copolymerized with a minor amount of functional groups such as an unsaturated carboxylic acid or an anhydride thereof may be used to provide a firm bond with an outer layer of nylon, PET, or polyurethane for example, while providing a low friction surface to the catheter lumen.

Specifically, the inner plastic layer may comprise a vinylic polymer which comprises from one to five mole percent of maleic anhydride polymer units, copolymerized preferably with ethylene to provide a high density polyethylene having low friction characteristics.

The flexible plastic tubing of this invention is easily coextruded, to provide a catheter tubing which requires no separate PTFE or other low friction sleeve, or coating for a reduction in overall cost of manufacture of the catheter tubing of this invention.

The catheter tubing of this invention may be simply coextruded as a multiple tubular layer catheter, with the reactive polymer used in this invention being typically the innermost layer, with that innermost layer becoming chemically bonded during the coextrusion to an outer plastic layer which is made of a different material. Thus, normally incompatible plastic materials may be bonded together in the catheter tubing of this invention to provide both a firm bond and the desired characteristics of the respective materials selected.

For example, nylon and high density polyethylene are normally quite sealingly incompatible with each other. By this invention, a high density polyethylene copolymer serving as an inner catheter tubing layer may be firmly, covalently bonded to a nylon outer catheter layer, so that the nylon can provide desired stiffness to the catheter while still permitting flexibility, and the high density polyethylene inner layer can provide low friction to a guidewire or inner catheter. The chemical bonding between the two catheter layers can take place during the extrusion process, or, if desired, subsequent heat treating or the like may be provided.

DESCRIPTION OF THE DRAWINGS

FIG. 1 is a perspective view of a PTCA balloon catheter in accordance with this invention;

FIG. 2 is an enlarged sectional view taken along line 2—2 of FIG. 1;

FIG. 3 is a schematic view of the extrusion of catheter tubing in accordance with this invention;

FIG. 4 is a longitudinal sectional view of another embodiment of a PTCA balloon catheter in accordance with this invention; and FIG. 5 is an enlarged transverse sectional view taken along line 5—5 of FIG. 4.

DESCRIPTION OF SPECIFIC EMBODIMENTS

Referring to FIGS. 1–3, an angioplasty catheter 10 is disclosed, which may be of conventional design and used for PTCA procedures except as otherwise indicated herein.

Catheter 10 defines a proximal end having a conventional hub 12.

Catheter 10 comprises an outer tubular body 14 which connects with the Y-connector at the proximal end 15, and also connects with a balloon 16 at its distal end 18. Outer catheter tube 14 terminates at its point of connection 18 with the proximal end of balloon 16.

Also, catheter 10 comprises an inner catheter tubing 20 which extends through the lumen of outer catheter tubing 14, defining a generally cylindrical space 22 between outer catheter tubing 14 and inner catheter tubing 20. Connector arm 24 of Y-connector 12 communicates in conventional manner with generally cylindrical space 22 at the proximal end thereof. Cylindrical space 22 extends along the catheter between catheter tubings 14 and 20, to terminate in communication with the interior of balloon 16. Inner catheter tubing 20, however, extends through balloon 16 as shown in FIG. 1, being sealed to balloon 16 at its distal end 26 in such a manner that the lumen 28 of inner catheter tubing 20 is open at its distal end. Second arm 30 of Y-connector 12 communicates with lumen 28 of inner catheter tubing 20, so that fluid communication is possible throughout the entire length of the catheter from connector arm 30 through the open distal end 26 of inner catheter tube 20, extending through balloon 16.

The above structure per se is used in commercially available prior art catheter designs.

In accordance with this invention, catheter 10 comprises a length of flexible plastic tubing which, in turn, comprises an outer plastic layer 32 and an inner plastic layer 34, the plastic materials of the outer and inner layers being different and chemically bonded to each other. While that specific plastic tubing is inner catheter tubing 20 in this specific embodiment, it could be used for the outer catheter tubing 14 as well. As an alternative, a bonding plastic layer could be placed both inside and outside of a catheter having a nylon middle layer, for example.

Outer tubular plastic layer 32 of catheter tube 20 may preferably be selected from the group consisting of nylon, polyurethane, and polyester, with such materials preferably being of greater stiffness than the material of inner tubular plastic layer 34.

Outer plastic layer 32 may typically comprise about 60 to 90 percent of the overall wall thickness of tube 20, providing a desired amount of stiffness to the tube while tube 20 retains a thin wall.

The material of inner tubular plastic layer 34 may be made of a material which exhibit lower frictional characteristics than the material of outer plastic layer 32, to facilitate the advancement of a guidewire or a separate, smaller catheter, for example, through the catheter of this invention, while at the same time enjoying the benefit of the physical properties provided to the catheter by the presence of and the physical properties of outer tubular layer 32.

Accordingly, for an angioplasty or angiography catheter, the overall catheter may exhibit a desired level of stiffness while still remaining flexible, due to the combined properties of inner and outer catheter tubes 20, 14. At the same time the frictional characteristics of the walls of lumen 28 may remain low irrespective of the frictional characteristics of layer 32. Furthermore, this may be accomplished without the separate addition of a PTFE sleeve, a coating, or the like in the catheter lumen, which requires a complexity in the manufacturing process. The layers of inner catheter tube 20 can be simply coextruded.

As previously stated, the material of the inner plastic layer 34 is preferably no more than half the overall thickness of the wall of inner catheter tubing 20, and it may be as low as about 5 or 10 percent of the overall thickness if desired. The material of inner plastic layer 34 is preferably a copolymer of a major amount of a vinylic polymer such as ethylene and a minor amount of an unsaturated carboxylic acid or an anhydride thereof, for example, a polyethylene which contains about 1 to 5 mole percent of maleic anhydride polymer units present in the molecule (on a mole percent basis).

More specifically, the material of inner plastic layer 34 may be a high density polyethylene, modified for example with the presence of about 1 or 2 mole percent of copolymerized maleic and anhydride units. As previously stated, such modified polyethylene resins are commercially available from the Quantum Chemical Corporation under the trademark Plexar, being used conventionally as tie layer resins for the bonding of dissimilar plastics together in coextruded films. However, nonreactive materials may be used for the inner layer 34 when coextrusion provides a physical bond of adequate strength with layer 32. Specific extrusion conditions for the best bonding depend on the product used.

In this invention, however, such materials as Plexar resins may be used in their own right as the second layer of this invention, to coat a layer of a catheter on the inside thereof to achieve the advantages previously described herein.

The functional groups which are found on the vinylic polymers used in this invention to promote a chemical bond between the outer and inner plastic layers may include copolymerized units such as an unsaturated carboxylic acid, or an anhydride thereof, or functional groups which are substituents of vinyl-containing molecules, polymerized or co-polymerized to form the vinylic polymer, for example hydroxyl in the case of polyvinyl alcohol, or other pendant reactive groups as may be desired to permit the formation of a chemical bond between two plastic materials.

The copolymerized, unsaturated carboxylic acid or anhydride thereof thus can serve as a functional group which bonds a vinylic polymer of the inner layer to the plastic of the outer layer. For example, particularly when the first layer is a polyamide such as nylon or another nitrogen-containing polymer such as polyurethane, this can be effectively accomplished. Similarly, such vinylic polymers having acid functional groups may react with hydroxyl-containing polymers of the outer layer, under proper reaction conditions. Such reactions may take place during co-extrusion of the two layers, to form a covalent bond between the outer and inner plastic layers of the catheter tubing as it is formed by the extrusion.

Preferably, inner plastic layer 34 is about 0.0005 to 0.003 inch thick while outer plastic layer 32 is about 0.003 to 0.006 inch thick, preferably giving a total wall thickness for the inner catheter tube 20 of 0.005 to 0.008 inch. The overall diameter of inner catheter tubing 20 is typically about 0.02 to 0.035 inch. Outer catheter tubing 14 has a typical wall thickness of about 0.003 to 0.005 inch, and a typical diameter of 0.04 to 0.05 inch, to provide a generally cylindrical space 22, although it is understood that inner tubing 20 is unconstrained and will not remain in exactly coaxial relationship with outer catheter tubing 14.

Inner catheter tubing 20 may be coextruded in generally conventional manner as schematically illustrated in FIG. 3. Extruder dies 36,37 bring cylindrical streams of molten plastic which are to form the outer layer 32 and inner layer 34 into coaxial, physical contact around mandrel 33, to pass through extruder die 35 while molten, to form catheter tubing 20. During this process, the reactive moieties of the plastic formulation which comprises inner layer 34 forms chemical bonds with the plastic of outer layer 32. Specifically, the nylon plastic of outer layer 32 is believed to react by forming amide-like linkages with the maleic anhydride units of the high density, copolymerized polyethylene plastic of layer 34 to form a strong bond between the layers. Then, the manufactured tubing 20 may be assembled in conventional manner to form the catheter of this invention, as disclosed herein.

High density polyethylene is generally understood by those skilled in the art to comprise a density of at least about 0.94 g./cc.. For purposes of this invention a polyethylene containing reactive groups and being of this density or greater is defined to be "high density polyethylene".

Referring to FIGS. 4 and 5, another embodiment of an intravascular balloon catheter in accordance with this invention is disclosed.

A catheter which comprises the conventional hub 12a similar to hub 12 is connected to the proximal end of double lumen tubing 40, which may be manufactured by an extrusion process in accordance with Fontirroche U.S. Pat. No. 5,063,018, modified to coextrude the tubing 40 disclosed herein. Tubing 40 comprises an outer layer or body 42, plus an inner layer 44 which may be added by coextrusion, typically in lumen 46, through which the guidewire extends.

The side arm 24a of hub 12a communicates with the other lumen 48 of tubing 40. The distal end of tubing 40 is sealed to a second length of flexible plastic tubing 50 which may be made of nylon or the like to have sufficient stiffness characteristics. Inner tubular layer 44 may be made of a material similar to inner tubular layer 34 of the previous embodiment for similar purposes. The outer catheter layer 42 may be similar to outer catheter layer 32 of the previous embodiment although possibly not of a material of greater stiffness than the material of layer 44 since the mass of material 42 in cross section is relatively greater. Basically the inventive principles described above still hold. The material of layer 42 is relied upon to provide desired stiffness to the catheter. The material of layer 44 provides desired low frictional characteristics to lumen 46, both of these being provided in a single catheter by a coextrusion process.

Tube 50 connects at its distal end to a catheter balloon 52. Lumen 48 communicates with the interior of balloon 52 through tube 50, communicating at the proximal end of lumen 48 with side arm 24a of the hub.

An inner catheter tube 54 is sealed to the distal end of lumen 46 and extends proximally through balloon 52 to be also sealed to the balloon at the distal catheter end 56. Tubing 54 may be similar in structure to tubing 20 of the previous embodiment, having an inner layer and an outer layer analogous to layers 32, 34 to perform the desired functions thereof as described above.

Thus, two different embodiments of a catheter are disclosed which may be of a desired stiffness and having a desired sealing compatibility to a catheter balloon 16 or 52, for example. At the same time, a catheter lumen similar to lumen 28 or 46 may have a low friction wall made of a different material bonded, and preferably covalently bonded, to the plastic of tube 32 or 42.

The above has been offered for illustrative purposes only, and is not intended to limit the scope of the invention of this application, which is as defined in the claims below.

That which is claimed is:

1. An intravascular catheter which comprises a coextruded length of flexible plastic extending most of the length of said catheter tubing, said tubing comprising an outer plastic layer and an inner plastic layer, said inner plastic layer comprising a high density polyethylene having functional groups chemically bonded to the material of the outer plastic layer, the plastic materials of said outer and inner plastic layers being different, the material of the inner plastic layer defining a catheter lumen, the walls of which exhibit lower frictional characteristics than the material of said outer plastic layer, the material of the outer plastic layer having greater stiffness than the material of the inner plastic layer.

2. The catheter of claim 1 in which the material of said outer plastic layer is selected from the group consisting of nylon, polyurethane, and polyester.

3. The catheter of claim 2 in which said inner plastic layer comprises from 30 to 50 percent of the thickness of said flexible plastic tubing.

4. The catheter of claim 3 in which said length of flexible plastic tubing and outer plastic layer comprise a length of multiple lumen tubing, said inner plastic layer comprising a tubular member extending through one of said lumens.

5. The catheter of claim 1 in which said high density polyethylene is a copolymer of a major amount of ethylene and a minor amount of an unsaturated carboxylic acid or an anhydride thereof.

6. The catheter of claim 5 in which the material of said outer plastic layer consists essentially of nylon.

7. The catheter of claim 1 in which said length of flexible plastic tubing and outer plastic layer comprise a length of multiple lumen tubing, said inner plastic layer comprising a tubular member extending through one of said lumens.

8. An intravascular catheter which comprises a length of flexible plastic tubing having a first lumen and extending most of the length of said catheter, said tubing comprising an outer plastic layer and an inner plastic layer, said inner plastic layer comprising a copolymer of a major amount of high density polyethylene and a minor amount of an unsaturated carboxylic acid or an anhydride thereof, the plastic materials of said outer and inner plastic layers being different, and chemically bonded to each other.

9. The catheter of claim 8 in which the material of the inner plastic layer defines a catheter lumen, the walls of which exhibit lower frictional characteristics than the material of said outer plastic layer.

10. The catheter of claim 8 in which the material of the outer plastic layer has greater stiffness than the material of the inner plastic layer.

11. The catheter of claim 8 in which from 1 to 5 mole percent of maleic anhydride polymer units are present in said high density polyethylene.

12. The catheter of claim 8 in which the material of said outer plastic layer comprises nylon.

13. The catheter of claim 8 in which said inner plastic layer has a thickness of 5 to 50 percent of the total wall thickness of said plastic tubing.

14. The catheter of claim 8 in which said length of flexible plastic tubing is surrounded by an outer length of flexible plastic tubing with a generally cylindrical space between said lengths of flexible plastic tubing.

15. The catheter of claim 8 in which said outer plastic layer defines a second lumen spaced from said inner plastic layer.

16. The catheter of claim 8 in which said length of flexible plastic tubing and outer plastic layer comprise a length of multiple lumen tubing, said inner plastic layer comprising a tubular member extending through one of said lumens.

17. An intravascular catheter which comprises a length of flexible plastic tubing having a plurality of lumens extending through the length of said plastic tubing, one of said lumens defining a lumen wall which carries an inner plastic layer chemically bonded to said lumen wall, the material of said inner plastic layer comprising a high density polyethylene in which from one to five mole percent of maleic anhydride polymer units are present, said inner plastic layer being chemically bonded to the material defining said one lumen wall, the plastic material of said tubing being different from the material of said inner plastic layer.

18. The catheter of claim 17 in which the material of said tubing having a plurality of lumens consists essentially of nylon.

* * * * *

UNITED STATES PATENT AND TRADEMARK OFFICE
Certificate

Patent No. 5,538,510                                    Patented: July 23, 1996

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Carlos A. Fontirroche, Miami Springs, FL; Stephen J. Querns, Boca Raton, FL; and Thomas N. Trotta, Miami Beach, FL.

Signed and Sealed this Thirteenth Day of December 2005.

NICHOLAS D. LUCCHESI
*Supervisory Patent Examiner*
Art Unit 3763